(12) United States Patent
Naglapura et al.

(10) Patent No.: US 11,426,226 B2
(45) Date of Patent: *Aug. 30, 2022

(54) ORTHOPEDIC SCREW EXTRACTOR

(71) Applicant: Shukla Medical, St. Petersburg, FL (US)

(72) Inventors: Subramanya Naglapura, St. Petersburg, FL (US); Alfred Litwak, St. Petersburg, FL (US)

(73) Assignee: Shukla Medical, St. Petersburg, FL (US)

( * ) Notice: Subject to any disclaimer, the term of this patent is extended or adjusted under 35 U.S.C. 154(b) by 366 days.

This patent is subject to a terminal disclaimer.

(21) Appl. No.: 16/673,415

(22) Filed: Nov. 4, 2019

(65) Prior Publication Data
US 2020/0060745 A1 Feb. 27, 2020

Related U.S. Application Data

(63) Continuation of application No. 15/585,044, filed on May 2, 2017, now Pat. No. 10,463,414.

(Continued)

(51) Int. Cl.
*A61B 17/88* (2006.01)
*A61B 17/86* (2006.01)
*B25B 27/18* (2006.01)
*B23B 51/08* (2006.01)
*B23B 51/00* (2006.01)

(52) U.S. Cl.
CPC .......... *A61B 17/8888* (2013.01); *B25B 27/18* (2013.01); *A61B 17/888* (2013.01); *A61B 17/8875* (2013.01); *A61B 17/8877* (2013.01); *B23B 51/0081* (2013.01); *B23B 51/08* (2013.01); *B23B 2251/64* (2013.01); *B23B 2251/66* (2013.01)

(58) Field of Classification Search
CPC .............. A61B 17/8888; A61B 17/888; A61B 17/8875; A61B 17/8877; B25B 27/18; B25B 27/14; B23B 2251/64; B23B 2251/66
USPC .......... 606/104, 315–317; 81/53.2, 459, 436; 254/18, 20; 408/22, 67, 223–225
See application file for complete search history.

(56) References Cited

U.S. PATENT DOCUMENTS 3,263,533 A * 8/1966 Carlson ................... B25B 27/18
  81/441
5,251,516 A * 10/1993 Desaulniers ............ B25B 27/18
  81/53.2

(Continued)

*Primary Examiner* — Marcela I. Shirsat
(74) *Attorney, Agent, or Firm* — Kim IP Law Group LLC

(57) ABSTRACT

An orthopedic screw extractor device including a shaft, an end portion about a first end of the shaft for securing to a handle, and a screw extracting tip about a second end of the shaft opposite the first end. The screw extracting tip further includes a generally frustoconical shape having a side at an angle of about 5 to 15 degrees relative to a longitudinal axis of the screw extracting tip. The screw extracting tip further includes first, second and third screw threads and first, second and third flutes circumferentially spaced about the screw extracting tip and extending across an entire length of the screw extracting tip. Each of the screw threads has a lead of about 0.07 to 0.12 inches, a pitch of about 0.02 to 0.04 inches, a thread angle of about 40 to 50 degrees, and a depth of about 0.01 to 0.02 inches.

21 Claims, 13 Drawing Sheets

Related U.S. Application Data

(60) Provisional application No. 62/330,777, filed on May 2, 2016.

(56) References Cited

U.S. PATENT DOCUMENTS

| | | | |
|---|---|---|---|
| 6,761,089 B2 * | 7/2004 | Bergamo | B25B 27/18 81/441 |
| 8,955,415 B2 * | 2/2015 | Lin | B25B 27/18 81/53.2 |
| D794,188 S * | 8/2017 | Naglapura | D24/133 |
| 10,463,414 B2 * | 11/2019 | Naglapura | B25B 27/18 |
| 2007/0093791 A1 * | 4/2007 | Happonen | A61B 17/8877 606/1 |
| 2016/0082579 A1 * | 3/2016 | Chen | B25B 27/18 81/441 |

* cited by examiner

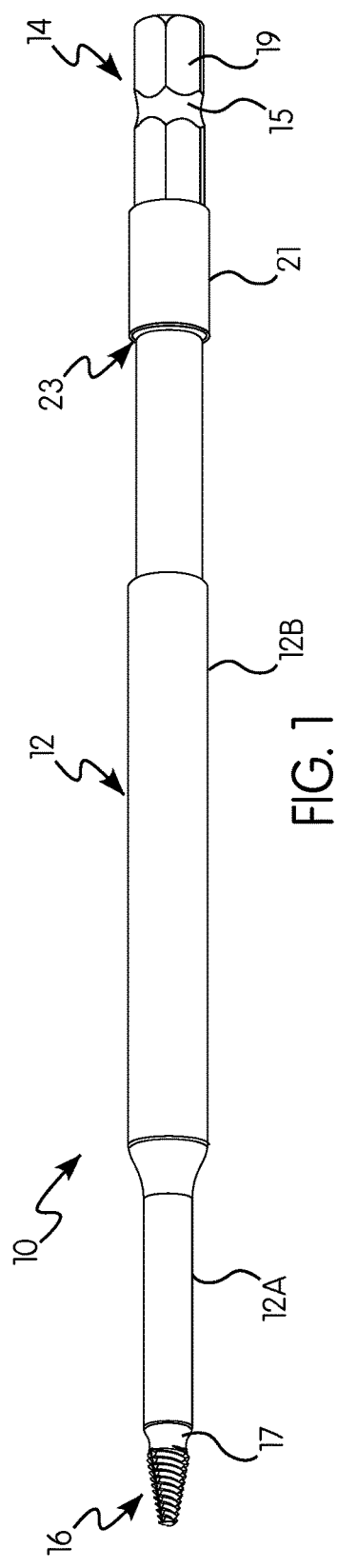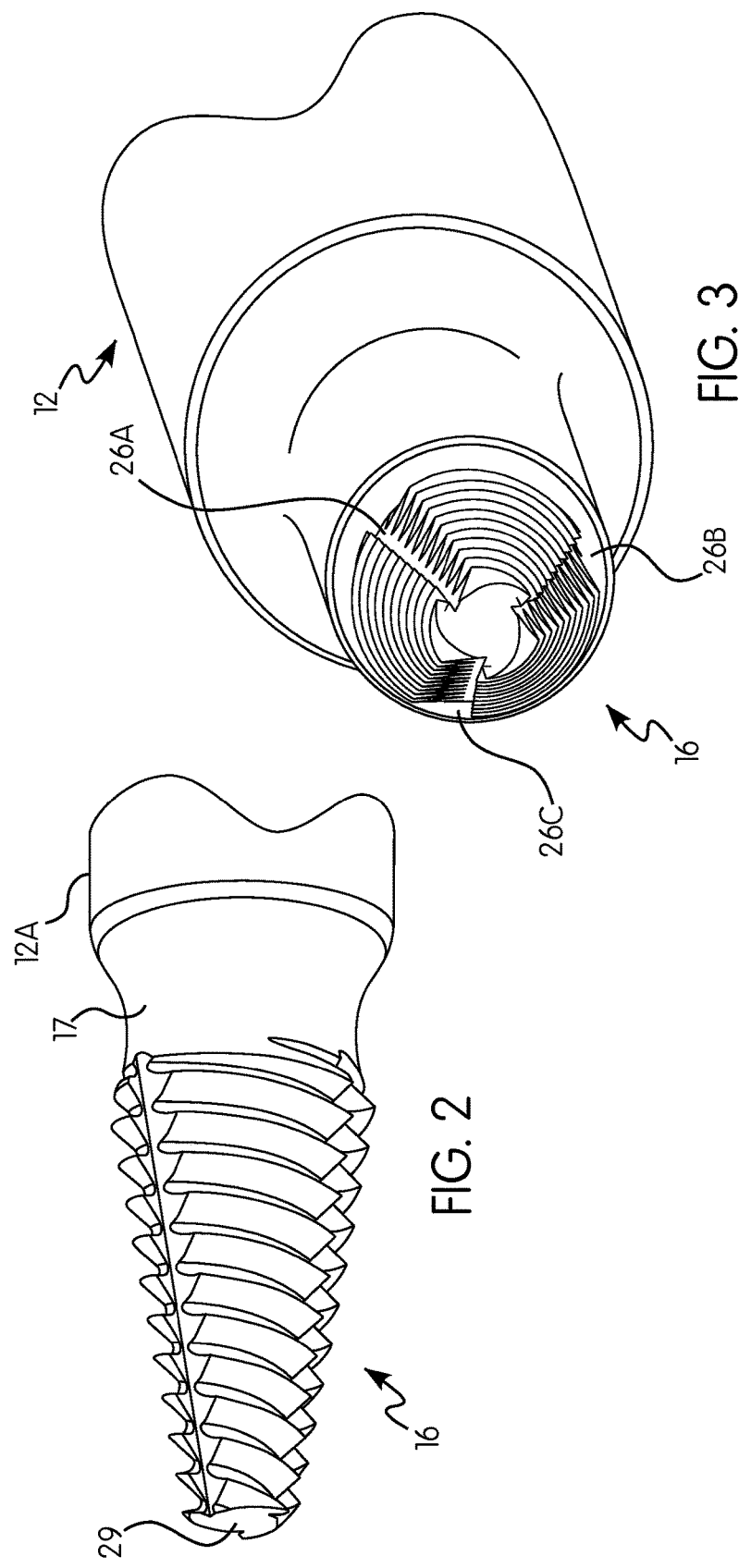
FIG. 1
FIG. 2
FIG. 3

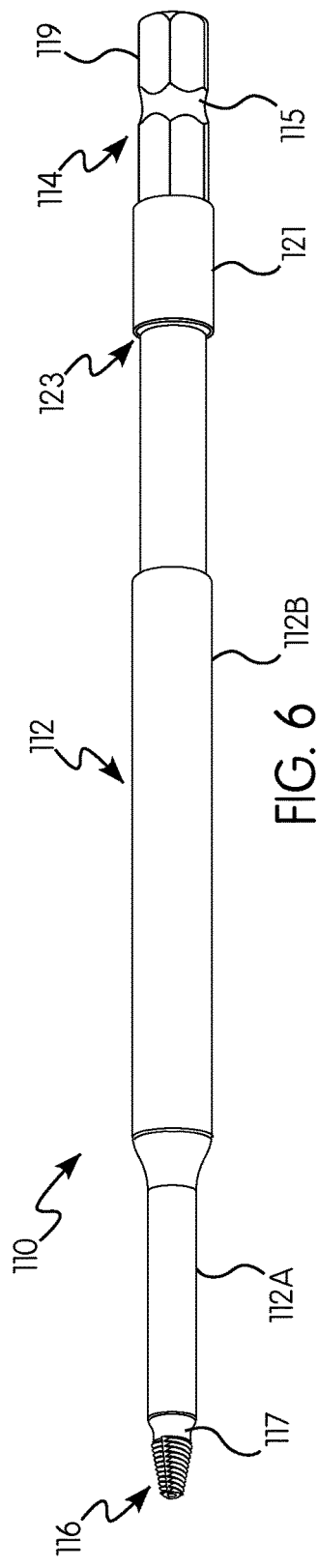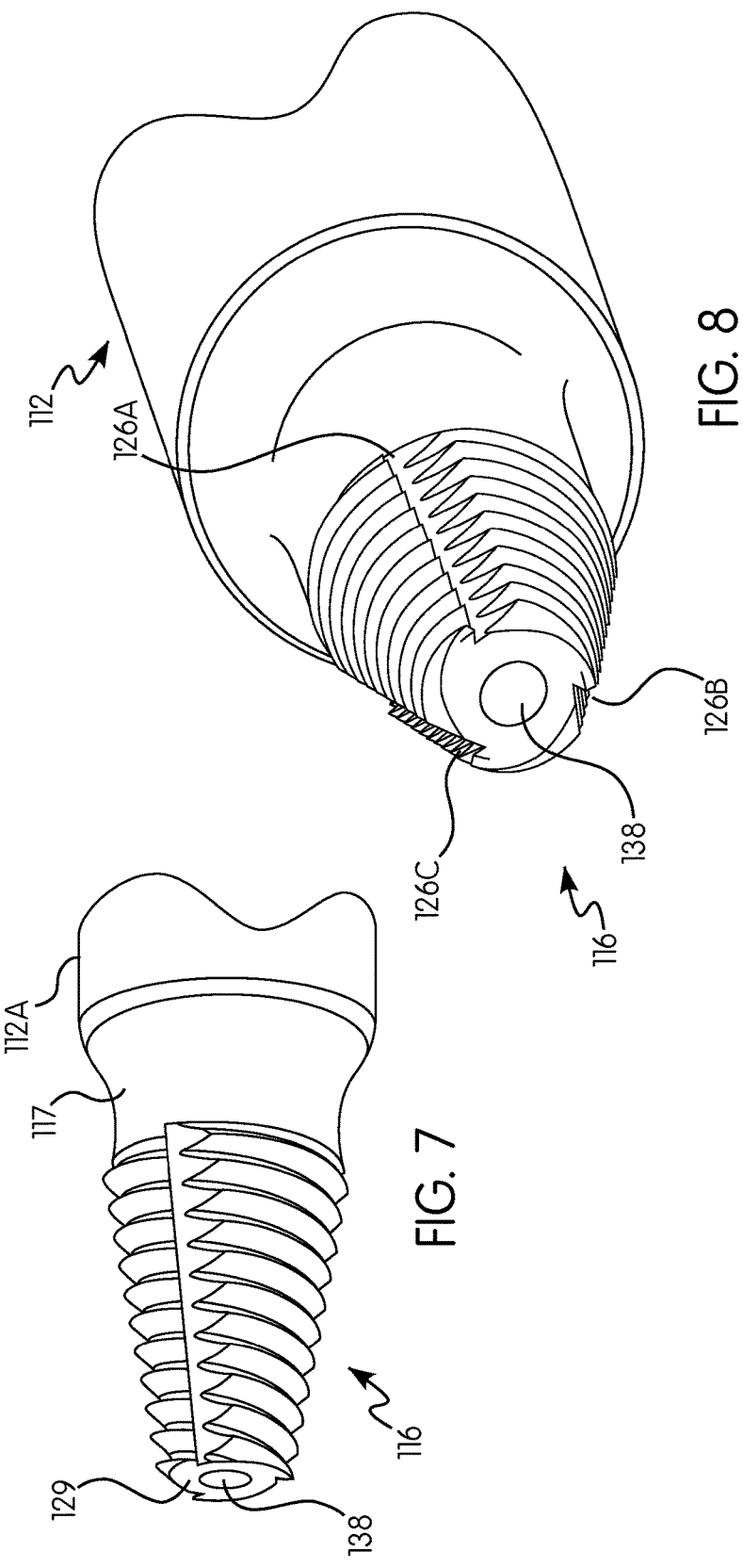

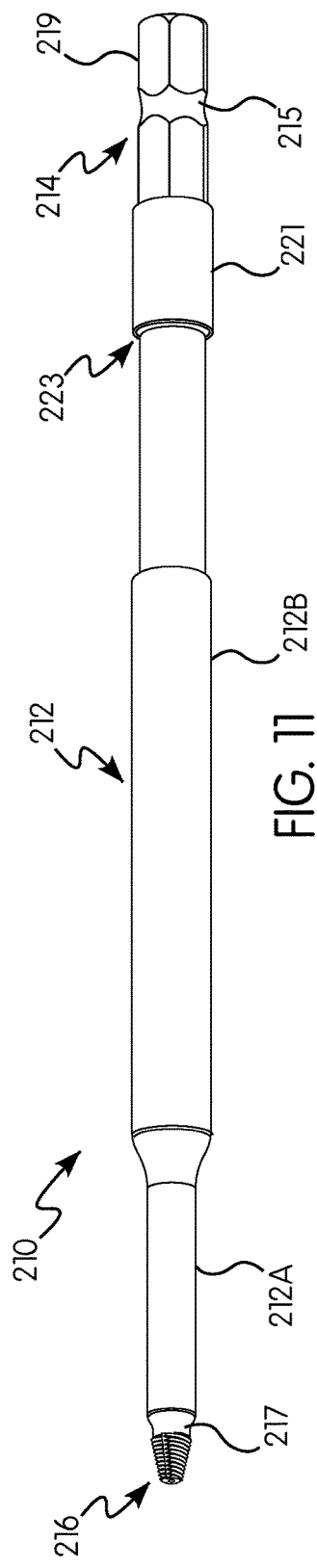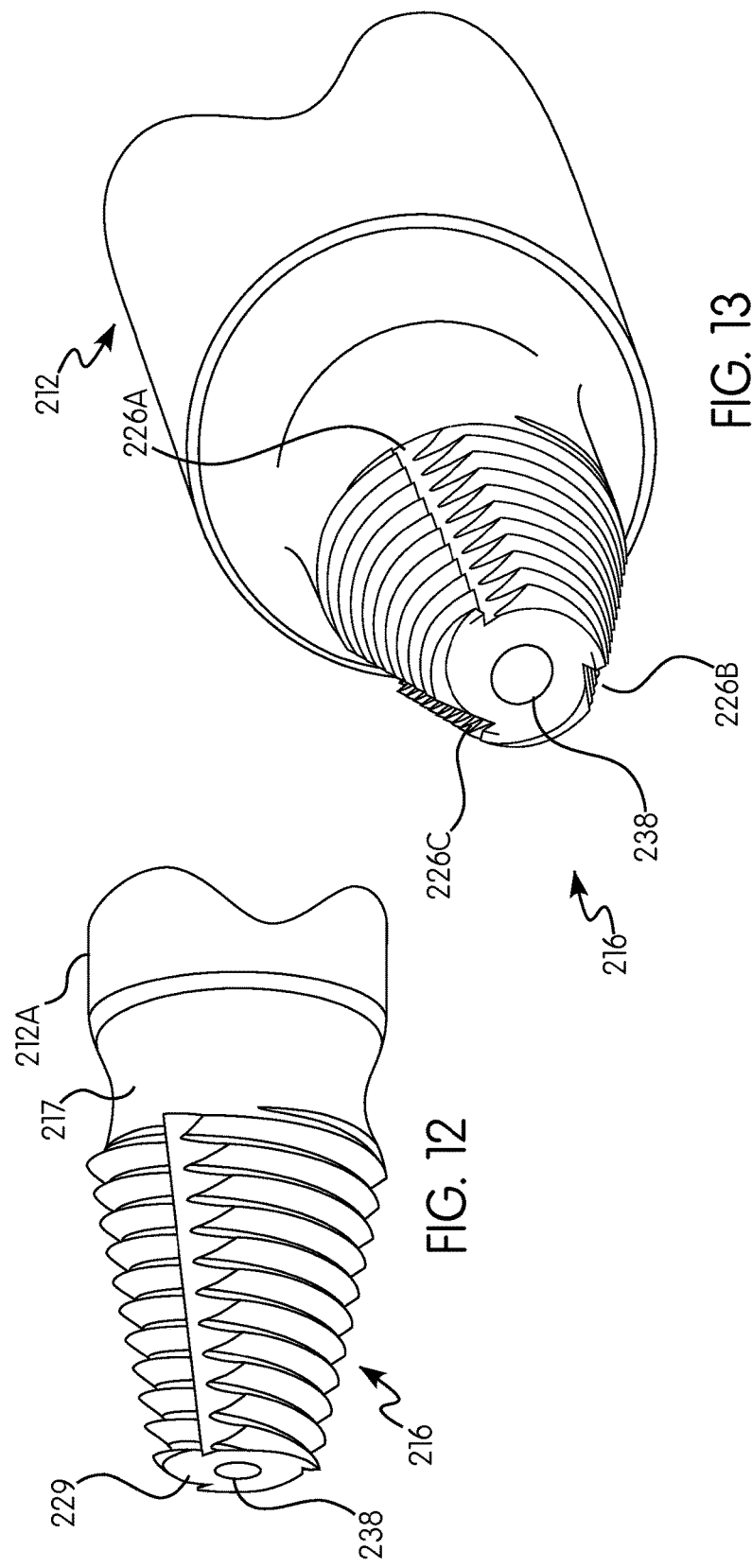

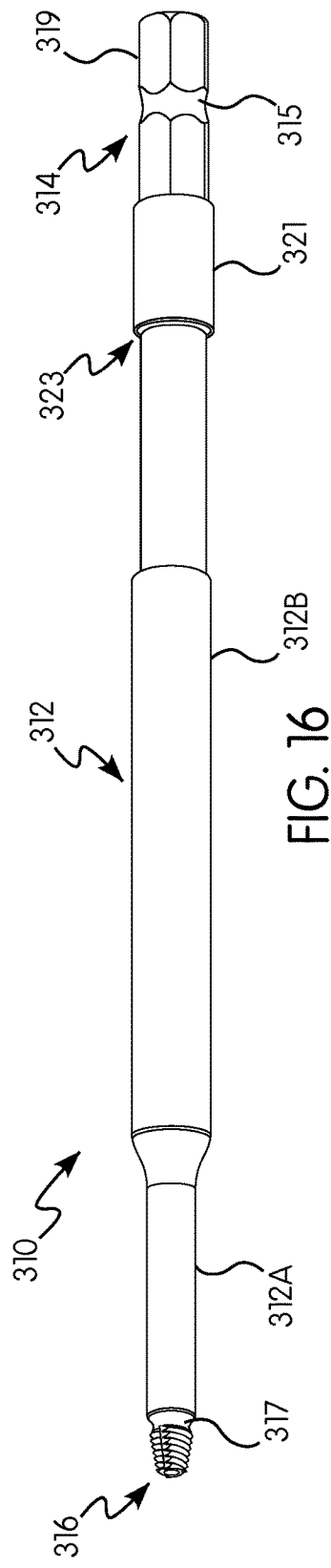
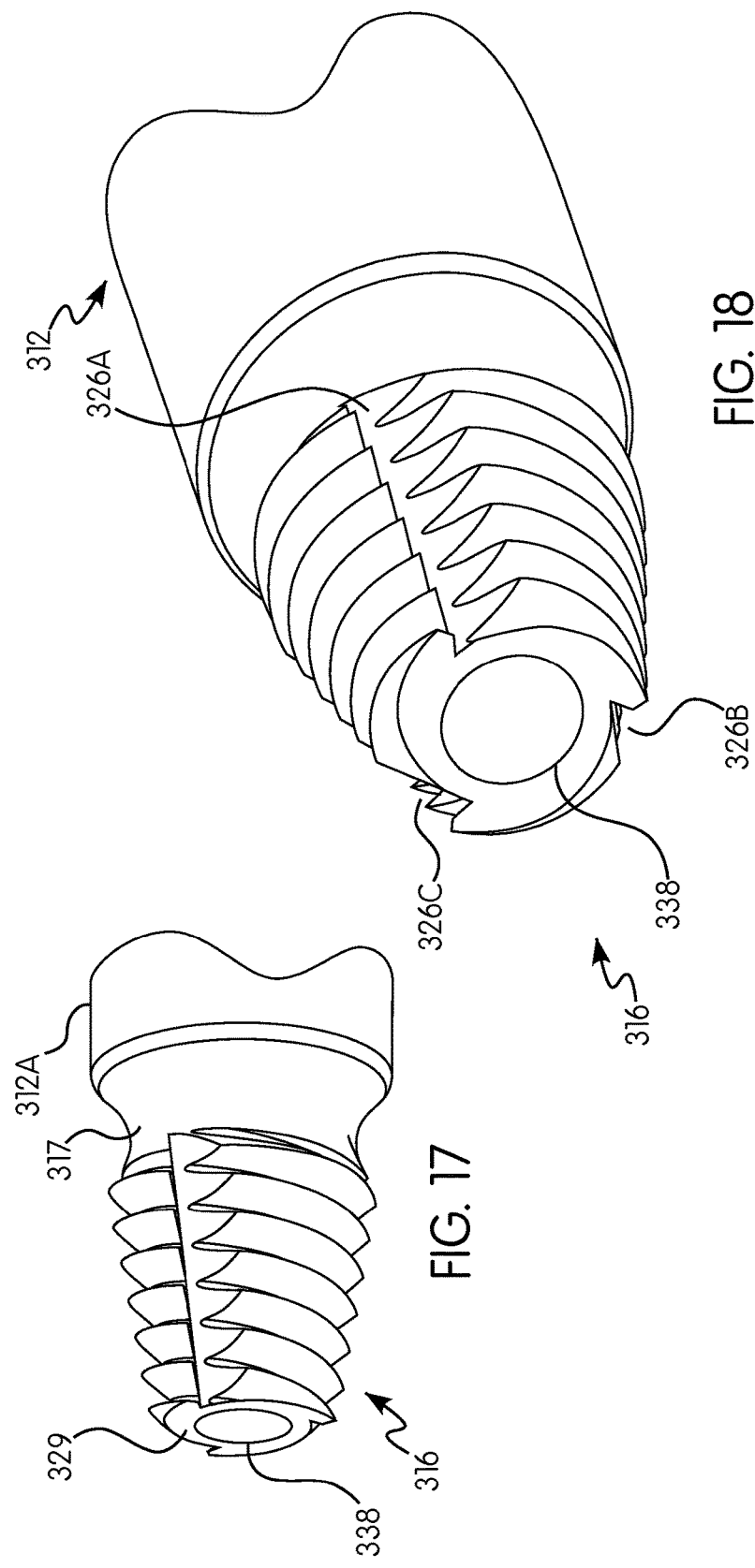

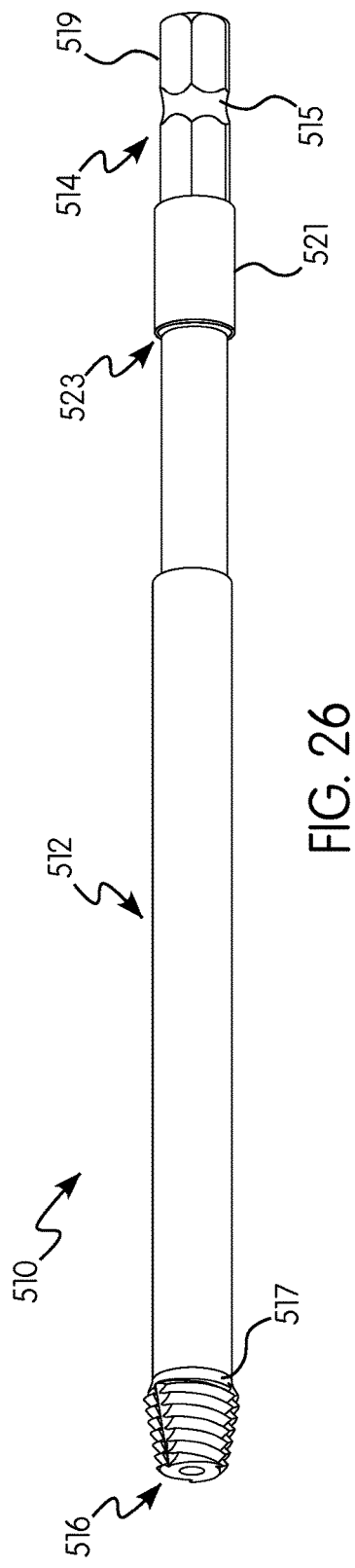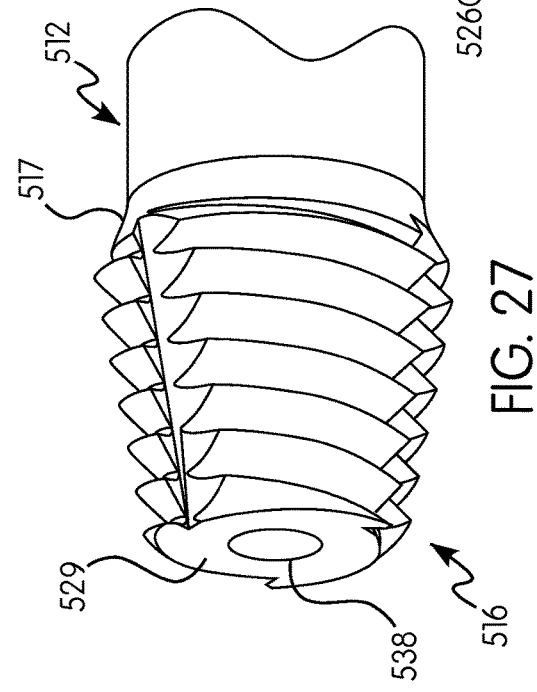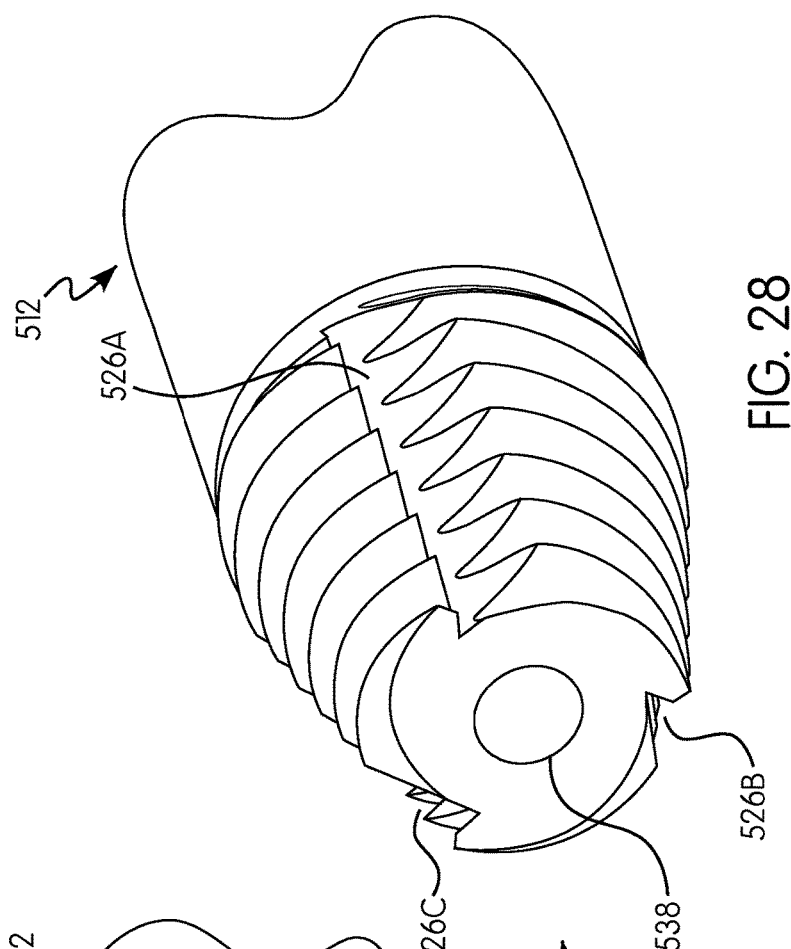

ORTHOPEDIC SCREW EXTRACTOR

CROSS-REFERENCE TO RELATED APPLICATIONS

This application claims the benefit of U.S. Provisional Application No. 62/330,777, filed May 2, 2016, the entire disclosure of which is incorporated by reference herein in its entirety.

BACKGROUND OF THE INVENTION

The present invention relates generally to the field of orthopedic surgical instruments. In particular, the present invention relates to an orthopedic screw extractor for removing damaged orthopedic fasteners, e.g., screws.

Bone screws are often used to anchor an orthopedic implant or to stabilize a bone in a patient. Occasionally, the bone screws in some patients will need to be removed or replaced by a surgeon. Such a procedure is particularly difficult when a screw is damaged. For example, a head of a bone screw can be stripped, thus making it difficult to remove from bone.

Conventional orthopedic screw extractors, however, do not provide sufficient bite to lock onto and extract a stripped or damaged screw. As a result, screw extraction is often difficult which can lead to excessive bone loss.

Thus, there is still a need for an orthopedic screw extractor that can sufficiently attach to and remove a damaged fastener or screw in a safe and efficient manner. Such a need is satisfied by the orthopedic screw extractor of the present invention.

BRIEF SUMMARY OF THE INVENTION

In accordance with an exemplary embodiment, the present invention provides an orthopedic screw extractor having a shaft, an end portion about a first end of the shaft for securing to a handle, and a screw extracting tip about a second end of the shaft opposite the first end. The screw extracting tip includes a generally frustoconical shape having a side at an angle of about 5 to 15 degrees relative to a longitudinal axis of the screw extracting tip. The screw extracting tip further includes first, second and third screw threads, wherein each screw thread has a lead of about 0.07 to 0.12 inches, a pitch of about 0.02 to 0.04 inches, a thread angle of about 40 to 50 degrees, and a depth of about 0.01 to 0.02 inches. The screw extracting tip further includes first, second and third flutes circumferentially spaced about the screw extracting tip and extending across an entire length of the screw extracting tip.

In accordance with another exemplary embodiment, the present invention provides an orthopedic screw extractor having a shaft, an end portion about a first end of the shaft for securing to a handle, and a screw extracting tip about a second end of the shaft opposite the first end. The screw extracting tip includes a generally frustoconical shape having a side at an angle of about 10 degrees relative to a longitudinal axis of the screw extracting tip and a distal end having an overall diameter of about 0.19 inches. The screw extracting tip further includes first, second and third screw threads, wherein each screw thread has a lead of about 0.12 inches, a pitch of about 0.04 inches, a thread angle of about 45 degrees, and a depth of about 0.02 inches. The screw extracting tip further includes first, second and third flutes circumferentially spaced about the screw extracting tip and extending across an entire length of the screw extracting tip.

In accordance with yet another exemplary embodiment, the present invention provides an orthopedic screw extractor having a shaft, an end portion about a first end of the shaft for securing to a handle, and a screw extracting tip about a second end of the shaft opposite the first end. The screw extracting tip includes a generally frustoconical shape having a side at an angle of about 10 degrees relative to a longitudinal axis of the screw extracting tip, a distal end having an overall diameter of about 0.19 inches, and an overall longitudinal length of about 1.3 times the overall diameter of the distal end. The screw extracting tip further includes first, second and third screw threads, wherein each screw thread has a pitch of about 0.2 times the overall diameter of the distal end, a lead of about 0.6 times the overall diameter of the distal end, a thread angle of about 45 degrees, and a depth of about 0.1 times the overall diameter of the distal end. The screw extracting tip further includes first, second and third flutes circumferentially spaced about the screw extracting tip and extending across the length of the screw extracting tip.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a perspective view of an orthopedic screw extractor in accordance with an exemplary embodiment of the present invention;

FIG. 2 is a partial perspective view of a screw extracting tip of the orthopedic screw extractor of FIG. 1;

FIG. 3 is a partial front perspective view of the screw extracting tip of the orthopedic screw extractor of FIG. 1;

FIG. 6 is a perspective view of an orthopedic screw extractor in accordance with another exemplary embodiment of the present invention;

FIG. 7 is a partial perspective view of a screw extracting tip of the orthopedic screw extractor of FIG. 6;

FIG. 8 is a partial front perspective view of the screw extracting tip of the orthopedic screw extractor of FIG. 6;

FIG. 11 is a perspective view of an orthopedic screw extractor in accordance with yet another exemplary embodiment of the present invention;

FIG. 12 is a partial perspective view of a screw extracting tip of the orthopedic screw extractor of FIG. 11;

FIG. 13 is a partial front perspective view of the screw extracting tip of the orthopedic screw extractor of FIG. 11;

FIG. 16 is a perspective view of an orthopedic screw extractor in accordance with a further exemplary embodiment of the present invention;

FIG. 17 is a partial perspective view of a screw extracting tip of the orthopedic screw extractor of FIG. 16;

FIG. 18 is a partial front perspective view of the screw extracting tip of the orthopedic screw extractor of FIG. 16;

FIG. 26 is a perspective view of an orthopedic screw extractor in accordance with yet another exemplary embodiment of the present invention;

FIG. 27 is a partial perspective view of a screw extracting tip of the orthopedic screw extractor of FIG. 26;

FIG. 28 is a partial front perspective view of the screw extracting tip of the orthopedic screw extractor of FIG. 26;

DETAILED DESCRIPTION OF THE INVENTION

Figure 4:
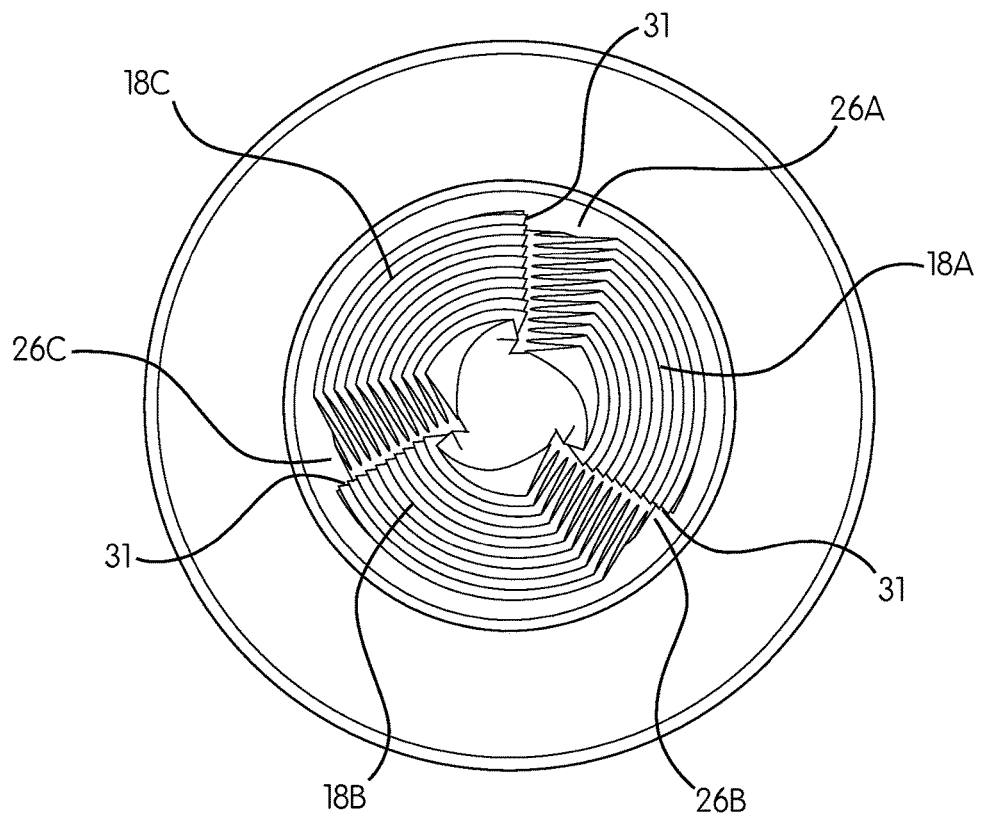
FIG. 4 is a front view of the screw extracting tip of the orthopedic screw extractor of FIG. 1.

Reference will now be made in detail to the various embodiments of the present invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, left, right, above, below and diagonal, are used with respect to the accompanying drawings. Such directional terms used in conjunction with the following description of the drawings should not be construed to limit the scope of the present invention in any manner not explicitly set forth.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the identified element and designated parts thereof. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various embodiments of the present invention can be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the embodiments of the present invention may be combined in any suitable manner in one or more embodiments. One skilled in the relevant art will recognize, in light of the description herein, that the present invention can be practiced without one or more of the specific features or advantages of a particular embodiment. In other instances, additional features and advantages may be recognized in certain embodiments that may not be present in all embodiments of the present invention.

In accordance with exemplary embodiments of the present invention, there is provided an orthopedic screw extractor 10, 110, 210, 310, 410, 510 having a screw extracting tip 16, 116, 216, 316, 416, 516 configured as shown in FIGS. 1-31. It is to be understood that FIGS. 1-5 illustrate a single size of the orthopedic screw extractor 10 in accordance with an exemplary embodiment of the present invention. Multiple sizes are described based upon the size and features of a fastener, e.g. a screw, which is to be extracted by the orthopedic screw extractor 10. Accordingly, FIGS. 6-10, FIGS. 11-15, FIGS. 16-20, FIGS. 21-25, and FIGS. 26-31, respectively illustrate differently sized orthopedic screw extractors 10, 110, 210, 310, 410, 510 in accordance with exemplary embodiments of the present invention.

In general, the description of the exemplary embodiment of the orthopedic screw extractor 10 illustrated in FIGS. 1-5 apply to embodiments 10, 110, 210, 310, 410, 510. The distinction or difference between the exemplary embodiments 10, 110, 210, 310, 410, 510 is the dimensional features and characteristics of its screw extracting tip which, in turn, is associated with a particularly sized fastener, which is to be extracted by the particular sized orthopedic screw extractor of the present invention.

Referring now to FIGS. 1-5, the orthopedic screw extractor 10 includes a shaft 12, an end portion 14 about a first end of the shaft for securing to a handle, and a screw extracting tip 16 about a second end of the shaft 12 opposite the first end.

Figure 21:
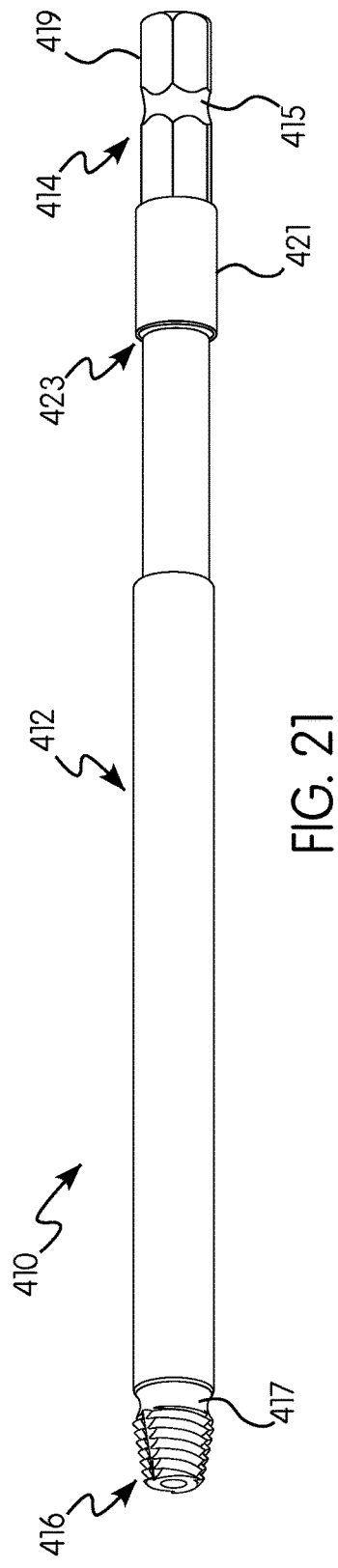
FIG. 21 is a perspective view of an orthopedic screw extractor in accordance with another exemplary embodiment of the present invention.
Figure 23:
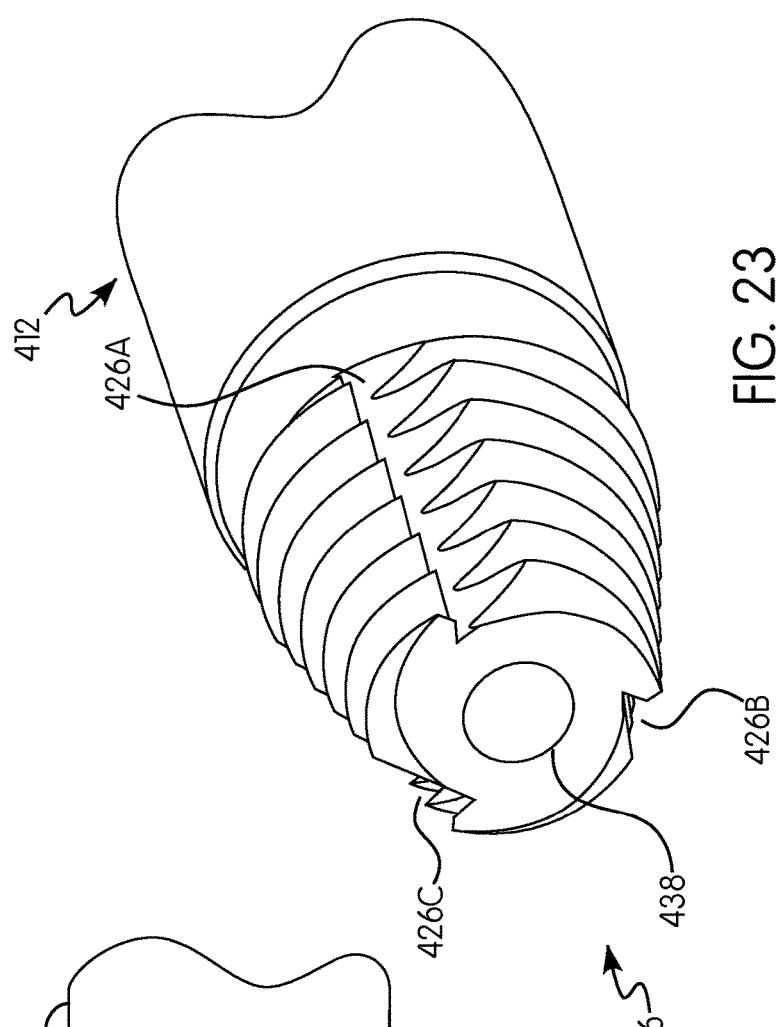
FIG. 23 is a partial front perspective view of the screw extracting tip of the orthopedic screw extractor of FIG. 21.
Figure 22:
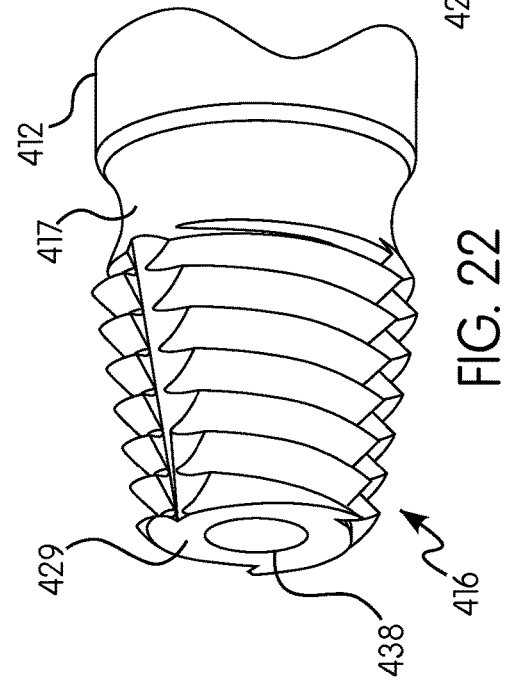
FIG. 22 is a partial perspective view of a screw extracting tip of the orthopedic screw extractor of FIG. 21.
Figure 24:
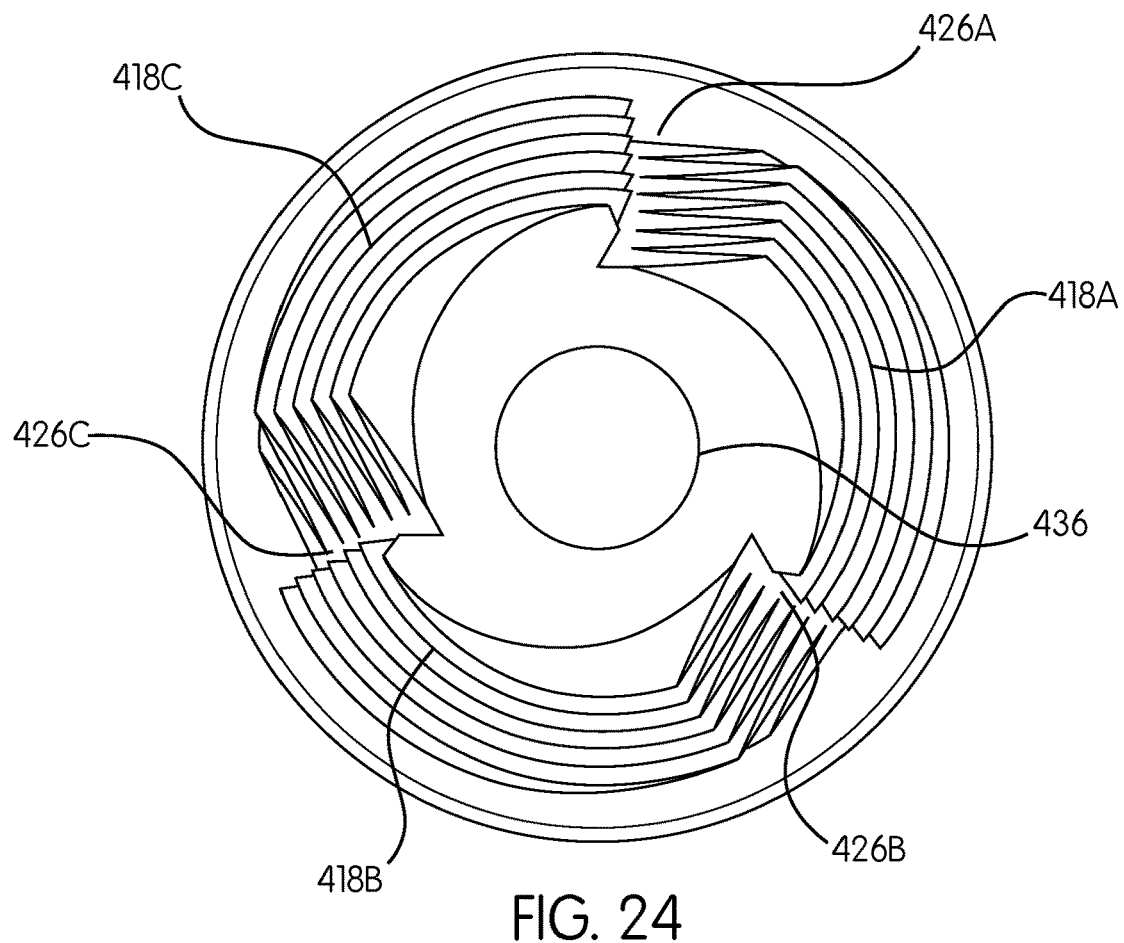
FIG. 24 is a front view of the screw extracting tip of the orthopedic screw extractor of FIG. 21.
Figure 25:
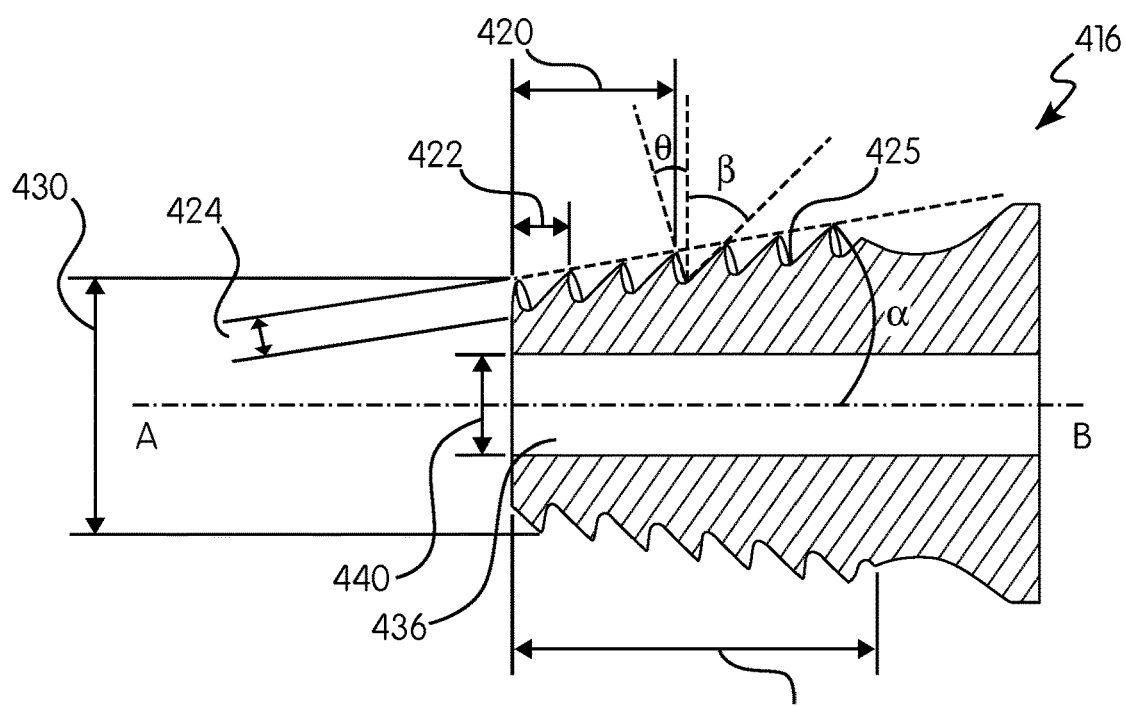
FIG. 25 is a partial cross-sectional view of the screw extracting tip of the orthopedic screw extractor of FIG. 21.
Figure 29:
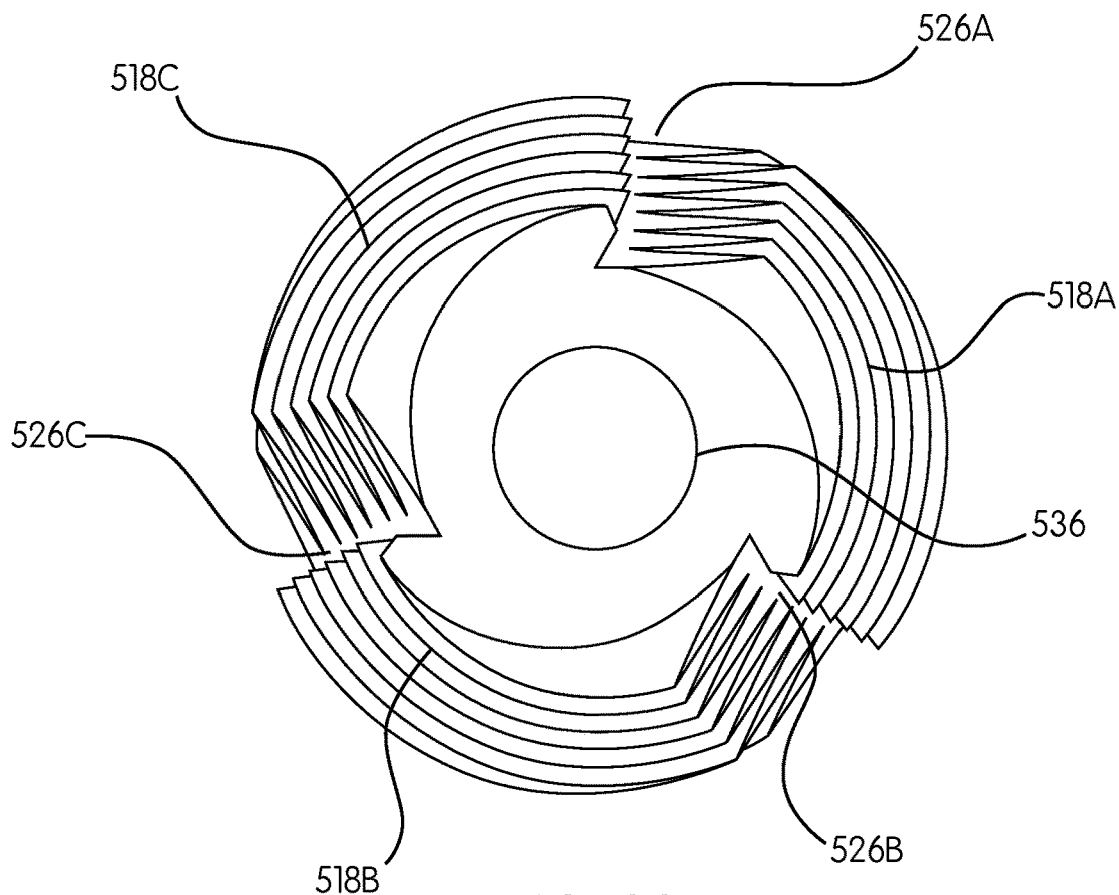
FIG. 29 is a front view of the screw extracting tip of the orthopedic screw extractor of FIG. 26.

The shaft 12 is generally an elongated member having a longitudinal central axis. The shaft 12 is preferably a cylindrical member having a circular cross section, however the shaft 12 can have any shape cross section such as hexagonal, polygonal or any other shape suitable for its intended purpose. The shaft 12 can be formed with a plurality of shaft segments 12A, 12B having different cross sectional diameters. For example, as shown in FIG. 1, shaft segment 12A has a cross sectional diameter less than a cross sectional diameter of shaft segment 12B. Alternatively, the shaft 12 can have a uniform cross sectional diameter as shown in FIGS. 16, 21 and 26.

The end portion 14 is configured to receive a tool or handle configured to impart rotating torque, including but not limited to a chuck, or collet (or some other means for imparting torque). As such, a cross sectional shape of the end portion 14 can be circular, hexagonal, polygonal or any other shape suitable for facilitating application of rotational torque to the screw extracting tip 16.

The end portion 14 preferably includes a hexagonal portion 19 proportioned to fit into a standard drill chuck or handle rotationally and axially. Additionally, the end portion 14 includes a necked portion 15 in order to help locate the orthopedic screw extractor in certain types of standard chucks or handles. In accordance with an aspect, a collar 21 may be provided so that a pry bar or the like may be positioned adjacent to necked portion 15 to apply a linear force at a bottom surface 23 of collar 21 to lift the orthopedic screw extractor 10 as a secondary aid to removal of a screw where necessary. Collar 21 preferably has a circular cross sectional shape that is uniformly accessible from any direction or rotational position of the orthopedic screw extractor 10 about its longitudinal axis to avoid unnecessary interference with adjacent objects.

As best shown in FIGS. 3 and 4, the screw extracting tip 16 is fluted, and has an overall generally frustoconical shape. A most distal end of the screw extracting tip has a generally transverse distal end surface 29 that is generally planar. The proximal or larger end of the screw extracting tip 16 terminates at a necked portion 17 adjacent the shaft 12. Specifically, necked portion 17 is positioned between the shaft 12 and the proximal end of the screw extracting tip 16 and facilitates locating the orthopedic screw extractor 10 in a chuck or handle.

Figure 5:
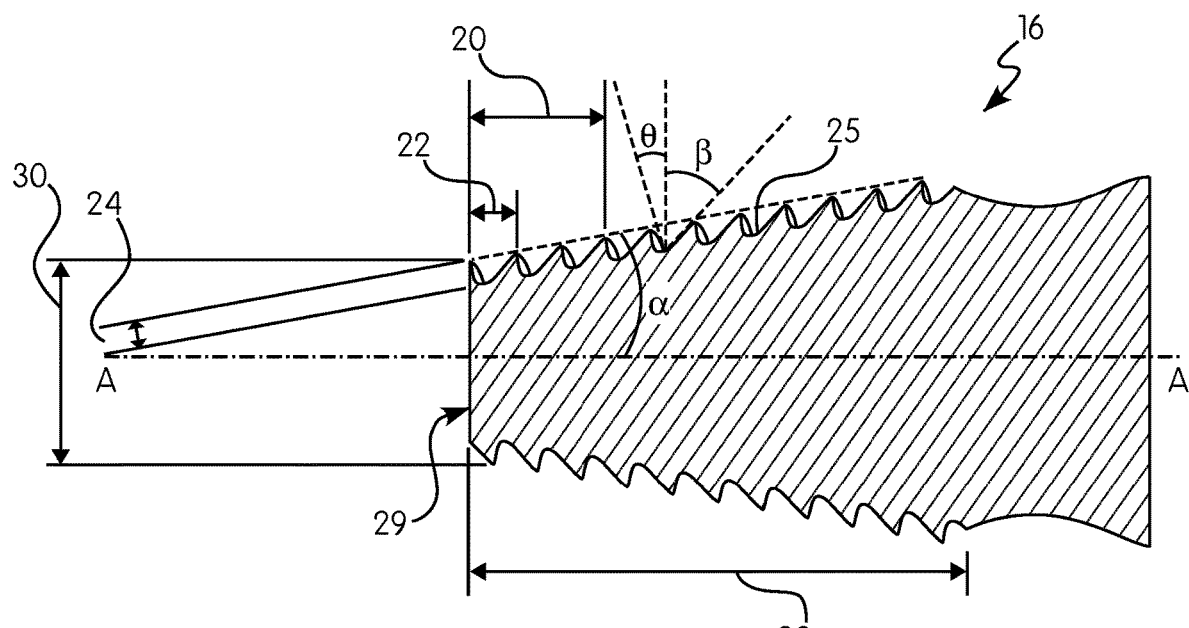
FIG. 5 is a partial cross-sectional view of the screw extracting tip of the orthopedic screw extractor of FIG. 1.
Figure 9:
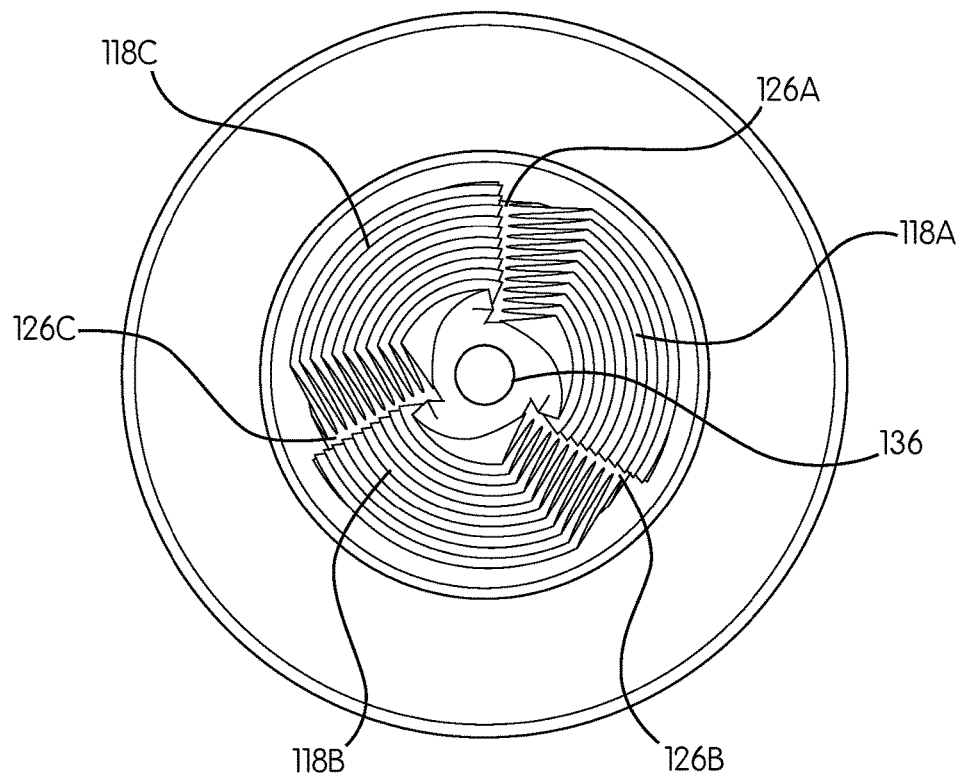
FIG. 9 is a front view of the screw extracting tip of the orthopedic screw extractor of FIG. 6.
Figure 10:
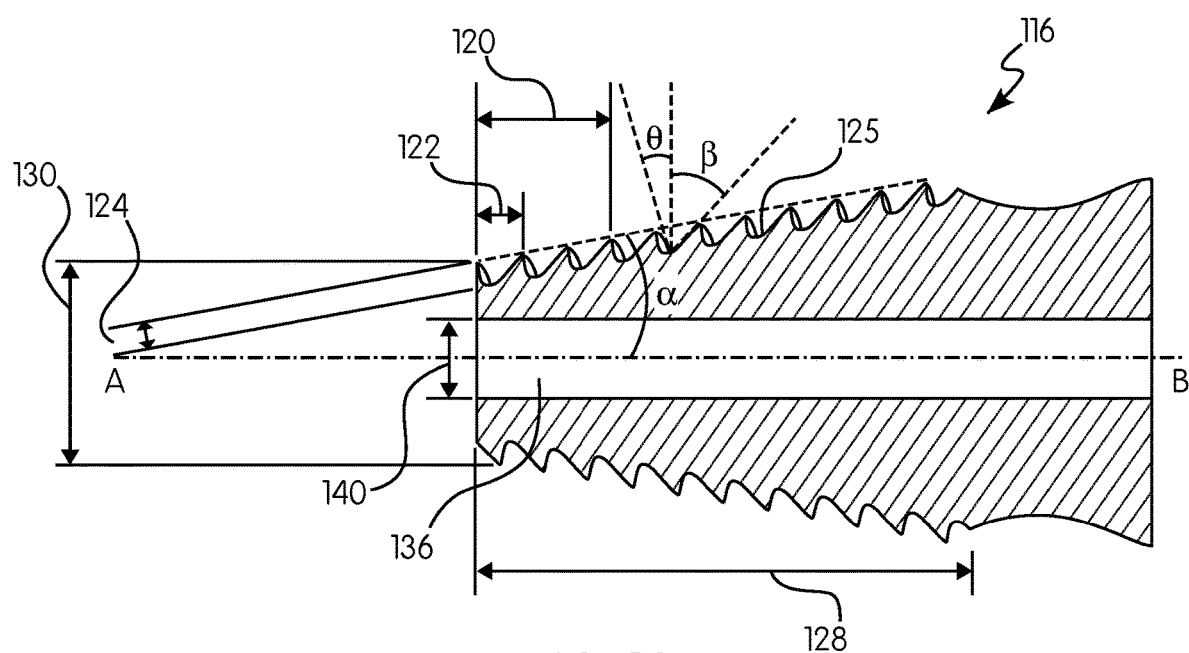
FIG. 10 is a partial cross-sectional view of the screw extracting tip of the orthopedic screw extractor of FIG. 6.
Figure 14:
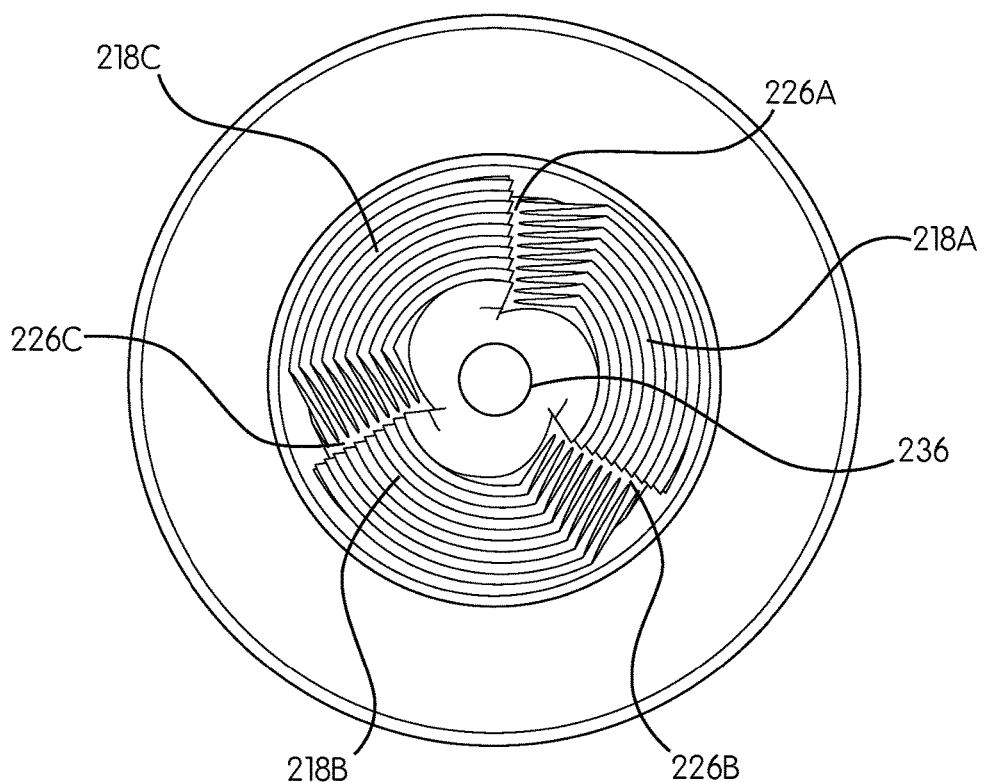
FIG. 14 is a front view of the screw extracting tip of the orthopedic screw extractor of FIG. 11.
Figure 15:
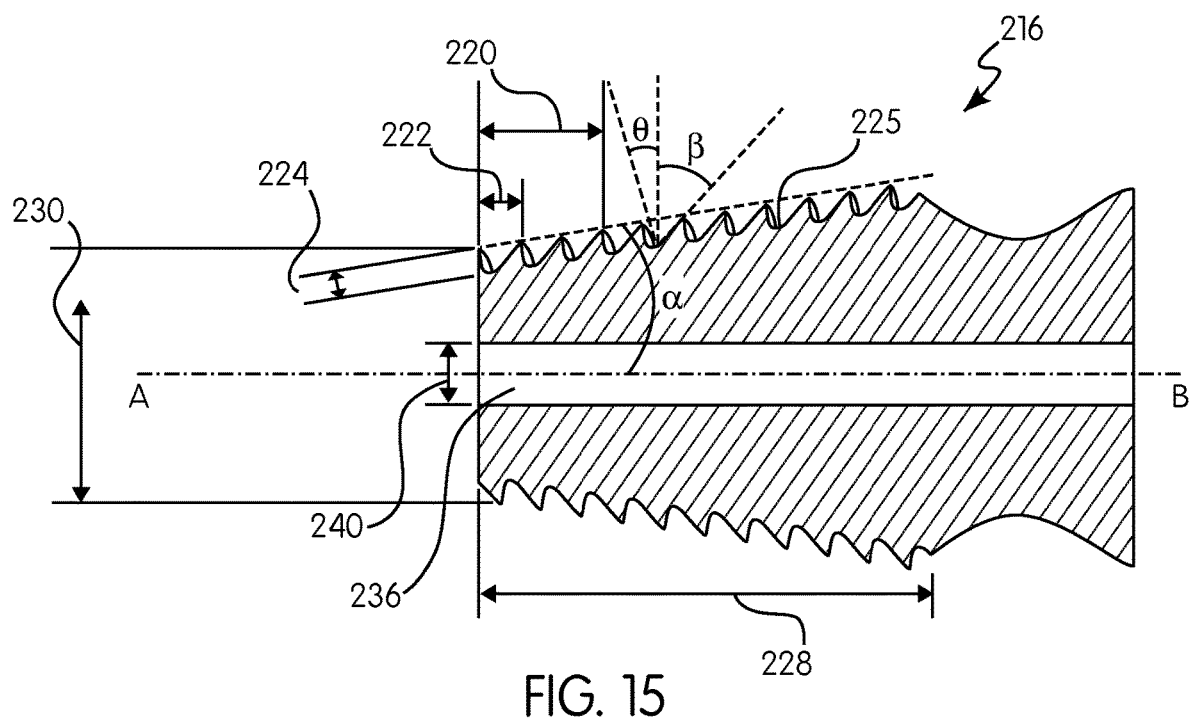
FIG. 15 is a partial cross-sectional view of the screw extracting tip of the orthopedic screw extractor of FIG. 11.
Figure 19:
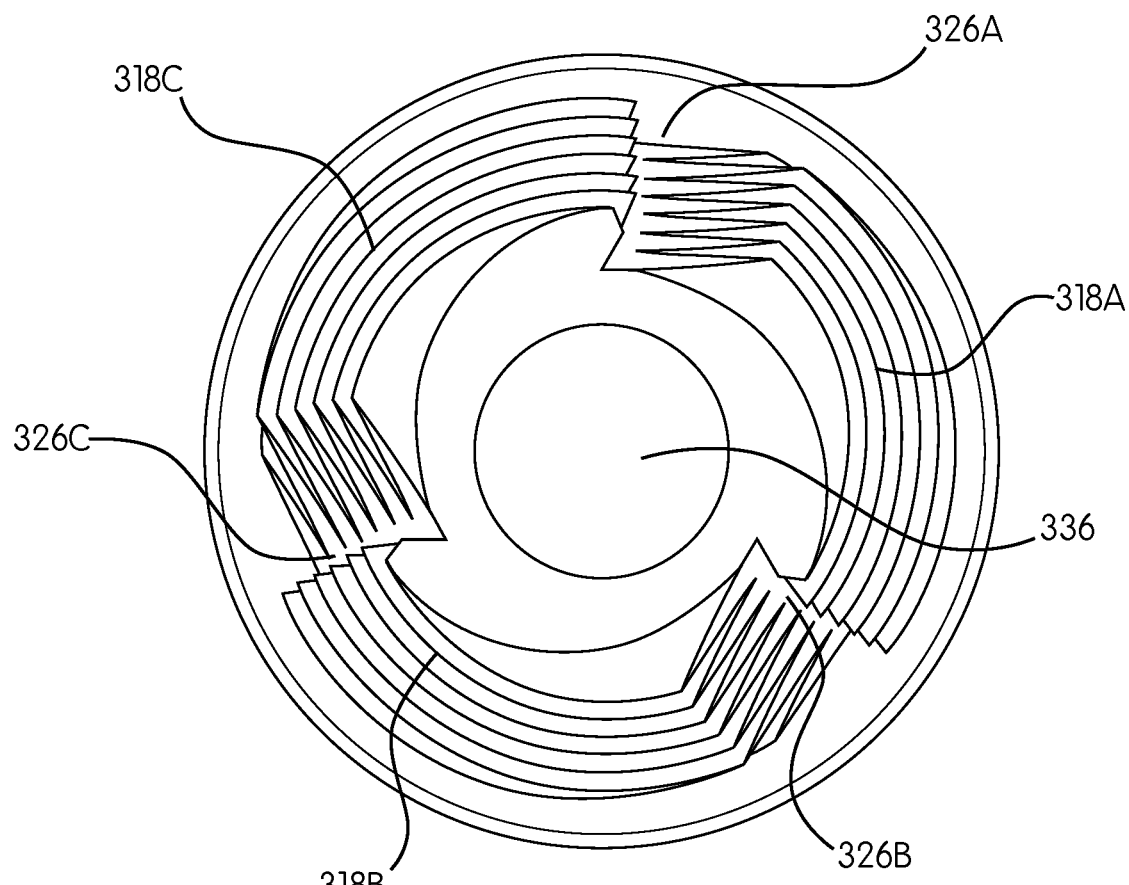
FIG. 19 is a front view of the screw extracting tip of the orthopedic screw extractor of FIG. 16.
Figure 20:
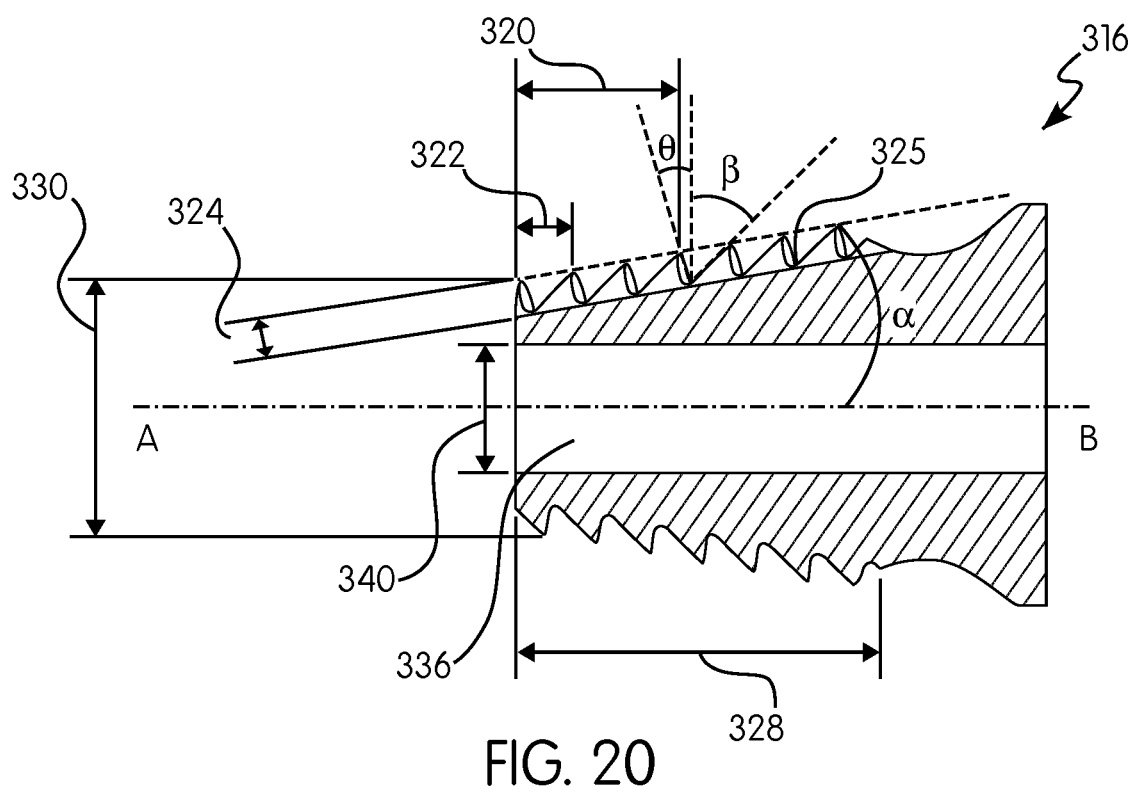
FIG. 20 is a partial cross-sectional view of the screw extracting tip of the orthopedic screw extractor of FIG. 16.

In sum, the screw extracting tip 16 has a tapered portion narrowing toward its distal end, that is, the end distal from the end portion 14. The tapered portion is frustoconical as shown in FIG. 5.

The screw extracting tip 16 is configured as a triple threaded screw (but alternatively may be configured as a single thread screw or a double threaded screw) having first, second and third screw threads 18A-C. As best shown in FIG. 4, each of the screw threads 18A-C are configured with sharpened edges 31. The screw threads 18A-C are left-hand threads formed about an exterior surface of the screw extracting tip 16. The left-hand screw threads 18A-C are helically oriented on the screw extracting tip 16 so as to screw into a screw well when a drill or handle is operated in a reverse or left hand direction.

The screw extracting tip 16 is designed to partially correspond with a screw well in a fastener or screw that is stripped. The orthopedic screw extractor 10 is designed to be impacted or driven at its end portion 14 to drive the screw extracting tip 16 into the screw well in a head of a screw until the orthopedic screw extractor 10 is locked onto the screw for extraction. In other words, the screw threads 18A-C are configured to engage the screw such that the orthopedic screw extractor 10 firmly grips the screw for extraction.

In accordance with an aspect of the exemplary embodiment, a side of the frustoconical shaped screw extracting tip 16 forms an acute taper angle $\alpha$ (FIG. 5) relative to the longitudinal central axis A of the screw extracting tip 16. Preferably, the taper angle $\alpha$ is about 5 to 15 degrees and more preferably about 10 degrees, but can alternatively be less than or greater than 10 degrees e.g., 8, 9, 11, 12 degrees.

In accordance with another aspect of the exemplary embodiment, the screw extracting tip 16 has an overall longitudinal length 28 of about 0.25 inches to about 0.27 inches, but can alternatively be less than about 0.25 inches or greater than about 0.27 inches e.g., +/−0.001, 0.010, 0.020, 0.030, 0.050 inches.

In accordance with yet another aspect of the exemplary embodiment, a distal end of the screw extracting tip 16 has an overall diameter 30 of about 0.07 inches to about 0.27 inches, but can alternatively be less than about 0.07 inches or greater than about 0.27 inches e.g., +/−0.001, 0.002, 0.003, 0.005, 0.010 inches. Generally, the overall diameter 30 of the distal end of the screw extracting tip 16 corresponds to a size of the fastener being extracted by the orthopedic screw extractor 10.

In accordance with an aspect of the exemplary embodiment, each of the first, second and third screw threads 18A-C are configured as buttress screw threads having a load angle $\theta$ of about 7 degrees, but can alternatively be less than or greater than 7 degrees e.g., 6 or 8 degrees and a thread angle $\beta$ of about 45 degrees, but can alternatively be less than or greater than 45 degrees e.g., 40 or 50 degrees.

In accordance with an aspect of the exemplary embodiment, each screw thread 18A-C has a lead 20 of about 0.07 inches to about 0.12 inches. Preferably, the lead 20 is about 0.07 inches, but can alternatively be less than or greater than 0.07 inches e.g., +/−0.001, 0.005, 0.010, 0.015 inches and the overall diameter 30 of the distal end of the screw extracting tip 16 is about 0.07 to 0.15 inches. In accordance with another aspect, the lead 20 is about 0.12 inches, but can alternatively be less than or greater than 0.12 inches e.g., +/−0.001, 0.010, 0.020, 0.030, 0.050 inches, and the overall diameter 30 of the distal end of the screw extracting tip 16 is about 0.18 to 0.27 inches.

In accordance with another aspect of the exemplary embodiment, each screw thread 18A-C has a pitch 22 of about 0.02 inches to about 0.04 inches. In accordance with an aspect, the pitch 22 is about 0.02 inches, but can alternatively be less than or greater than 0.02 inches e.g., +/−0.001, 0.002, 0.003, 0.004, 0.005 inches, and the overall diameter 30 of the distal end of the screw extracting tip 16 is about 0.07 to 0.15 inches. In accordance with another aspect, the pitch 22 is about 0.04 inches, but can alternatively be less than or greater than 0.04 inches e.g., +/−0.01, 0.001, 0.002, 0.003, 0.004, 0.005 inches, and the overall diameter 30 of the distal end of the screw extracting tip 16 is about 0.18 to 0.27 inches.

In accordance with yet another aspect of the exemplary embodiment, each screw thread 18A-C has a depth 24 of about 0.01 inches to about 0.02 inches. In accordance with an aspect, the depth 24 is about 0.01 inches, but can alternatively be less than or greater than 0.01 inches e.g., +/−0.001, 0.002, 0.003, 0.004, 0.005 inches, and the overall diameter 30 of the distal end of the screw extracting tip 16 is about 0.07 to 0.15 inches. In accordance with another aspect, the depth 24 is about 0.02 inches, but can alternatively be less than or greater than 0.02 inches e.g., +/−0.010, 0.001, 0.002, 0.003, 0.004, 0.005 inches, and the overall diameter 30 of the distal end of the screw extracting tip 16 is about 0.18 to 0.27 inches.

In accordance with another aspect of the exemplary embodiment, each screw thread 18A-C has a root radius 25 of about 0.005 inches, but can alternatively be less than or greater than 0.005 inches e.g., +/−0.001, 0.002, 0.003, 0.004 inches.

In accordance with an exemplary embodiment of the present invention, the screw extracting tip 16 includes a series of three generally equally sized and identically shaped uniform flutes 26A-C circumferentially spaced about the screw extracting tip 16 and extending across an entire length of the screw extracting tip 16. Preferably, the three flutes are distributed uniformly, radially about central longitudinal axis A of the screw extracting tip.

Figure 31:
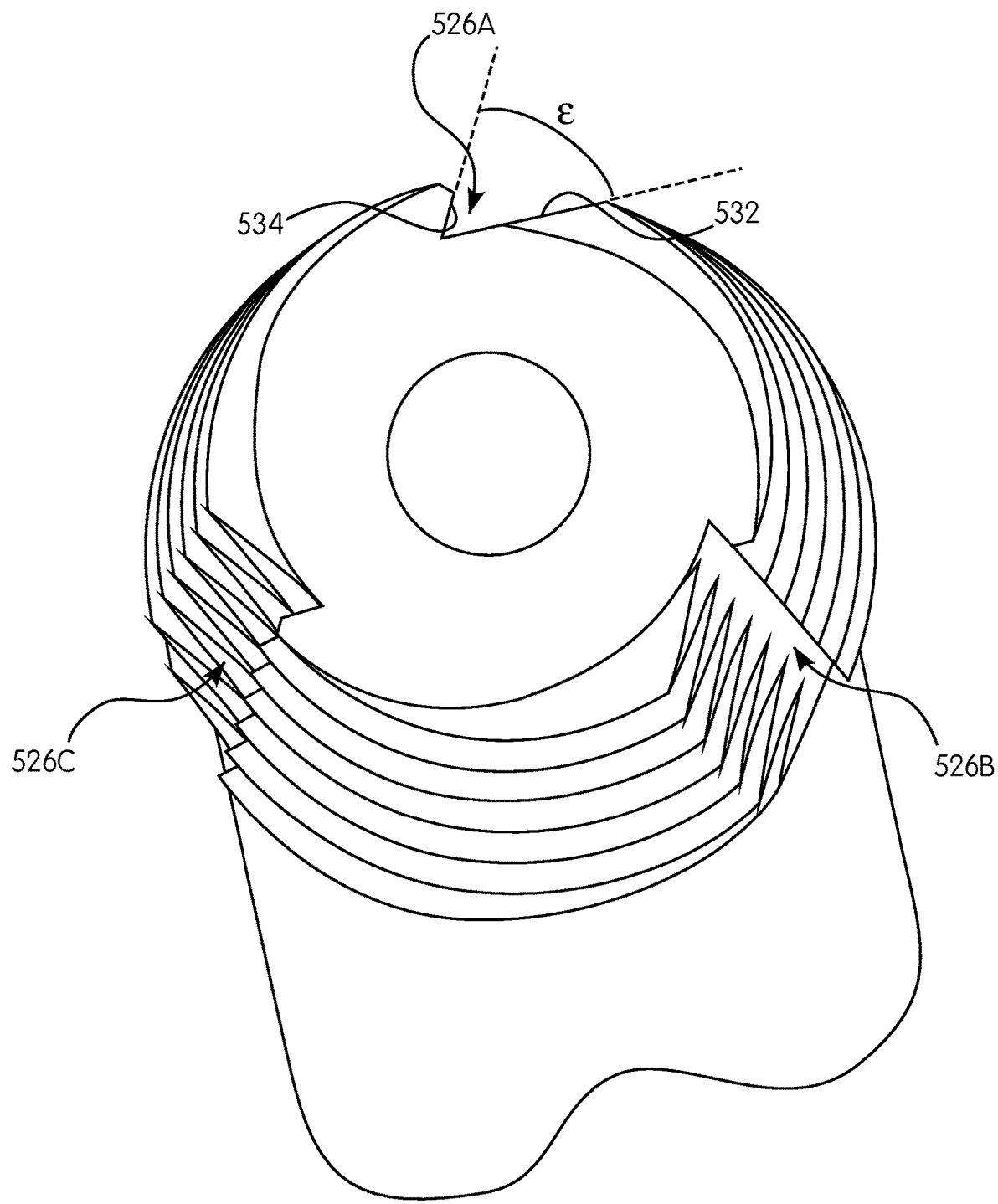
FIG. 31 is another partial front perspective view of the screw extracting tip of the orthopedic screw extractor of FIG. 26.

As shown in FIG. 31, for example, the screw extracting tip 516 has three uniform flutes 526A-C extending the entire longitudinal length of the screw extracting tip 516. Each flute 526A-C has a major planar surface 532 and a cutting surface 534 at an angle c from the major planar surface 532 of about 60 degrees, but can alternatively be less than or greater than 60 degrees e.g., 50, 55, 65, 70 degrees.

In accordance with another exemplary embodiment of the present invention illustrated in FIGS. 6-31, the orthopedic screw extractor 110, 210, 310, 410, 510 includes a cannulation 136, 236, 336, 436, 536, e.g., an axial counterbore opening extending inwardly from the flat planar distal end surface 129, 229, 329, 429, 529 along a longitudinal length of the shaft 112, 212, 312, 412, 512. The cannulation opening 138, 238, 338, 438, 538 provides clearance for an axial protrusion incorporated in a drive opening in a head end of a fastener or screw intended to be removed. The cannulation 136, 236, 336, 436, 536 also provides receipt and storage of shards or other materials that may lodge within a drive opening or a head of a screw which is being extracted by the orthopedic screw extractor 110, 210, 310, 410, 510. The cannulation 136, 236, 336, 436, 536 is generally a cylindrical counterbore having a circular cross section, however the cannulation 136, 236, 336, 436, 536 can have any cross sectional shape such as hexagonal, polygonal and the like.

Figure 30:
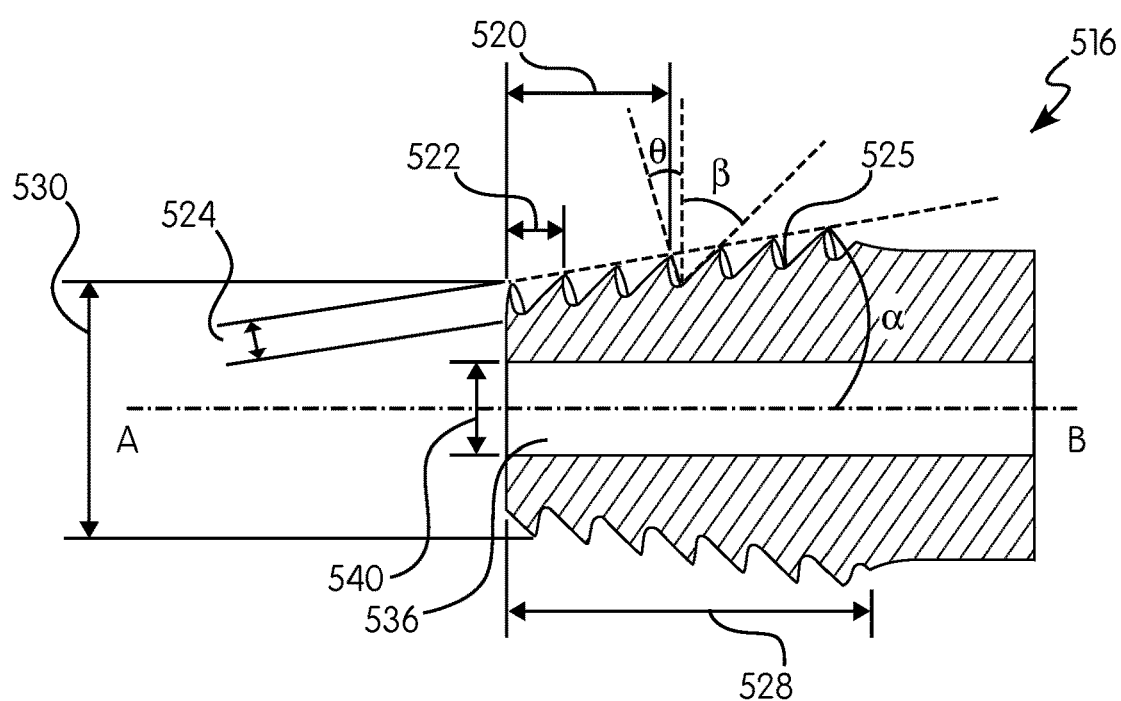
FIG. 30 is a partial cross-sectional view of the screw extracting tip of the orthopedic screw extractor of FIG. 26.

As shown in FIG. 30, the cannulation 536 extends along a longitudinal axis B of the shaft 512. For purposes of clarity, it is to be understood that central longitudinal axis A and longitudinal axis B are collinear. In accordance with an aspect, the cannulation 536 extends through the screw extracting tip 516 forming the opening 538 about the distal end surface 529 of the screw extracting tip 516 (FIG. 28). The cannulation 136, 236, 336, 436, 536 has an overall diameter 140, 240, 340, 440, 540 of about 0.04 inches to about 0.11 inches, but can alternatively be less than about 0.04 inches or greater than about 0.11 inches e.g., +/−0.001, 0.002, 0.003, 0.004, 0.005, 0.010 inches.

In accordance with another aspect of the exemplary embodiment, the screw extracting tip 16 has a coating that provides better fixation of the orthopedic screw extractor 10 to the screw being removed. Preferably, the screw extracting tip 16 is coated with a titanium nitride (TiN) coating or aluminum titanium nitride (AlTiN) coating to allow the threads to better engage a screw well of the screw and allow for more torque to be applied.

Attached as TABLE 1 is a summary of various dimensions and angular limitations of the orthopedic screw extractor embodiments 10, 110, 210, 310, 410, 510 described above and illustrated in FIGS. 1-31 wherein the dimensions of each orthopedic screw extractor set forth correspond to various screw sizes.

TABLE 1

|  | 2 mm Extractor (FIGS. 1-5) | 3 mm Extractor (FIGS. 6-10) | 4 mm Extractor (FIGS. 11-15) | 5 mm Extractor (FIGS. 16-20) | 6 mm Extractor (FIGS. 21-25) | 7 mm Extractor (FIGS. 26-31) |
|---|---|---|---|---|---|---|
| Diameter of Distal End | 0.05"-0.09" | 0.09"-0.13" | 0.12"-0.16" | 0.16"-0.20" | 0.20"-0.24" | 0.25"-0.29" |
| Longitudinal Length | 0.24"-0.28" | 0.24"-0.28" | 0.23"-0.27" | 0.23"-0.27" | 0.23"-0.27" | 0.23"-0.27" |
| Taper Angle ($\alpha$) | 5°-15° | 5°-15° | 5°-15° | 5°-15° | 5°-15° | 5°-15° |
| Thread Angle ($\beta$) | 40°-50° | 40°-50° | 40°-50° | 40°-50° | 40°-50° | 40°-50° |
| Lead | 0.05"-0.09" | 0.05"-0.09" | 0.05"-0.09" | 0.10"-0.14" | 0.10"-0.14" | 0.10"-0.14" |
| Pitch | 0.01"-0.03" | 0.01"-0.03" | 0.01"-0.03" | 0.03"-0.05" | 0.03"-0.05" | 0.03"-0.05" |
| Depth | 0.005"-0.015" | 0.005"-0.015" | 0.005"-0.015" | 0.01"-0.03" | 0.01"-0.03" | 0.01"-0.03" |
| Cannulation Diameter | N/A | 0.04"-0.11" | 0.04"-0.11" | 0.04"-0.11" | 0.04"-0.11" | 0.04"-0.11" |

In accordance with an aspect of the exemplary embodiments of the present invention illustrated in FIGS. 1-31, a ratio of the lead 20 to the pitch 22 for each screw thread 18A-C is about 3:1, but can alternatively be less than or greater than 3:1 e.g., 2.8:1, 2.9:1, 3.1:1 and 3.2:1.

In accordance with another aspect of the exemplary embodiment, a ratio of the pitch 22 to the depth 24 for each screw thread 18A-C ranges from about 1.7:1 to 1.9:1, but can alternatively be less than 1.7:1 or greater than 1.9:1 e.g., 1.5:1, 1.6:1, 2.0:1, 2.1:1).

In accordance with yet another aspect of the exemplary embodiment, a ratio of the depth 24 to the overall diameter 30 of a distal end of the screw extracting tip 16 for each screw thread 18A-C ranges from about 0.09:1 to 0.19:1, but can alternatively be less than 0.09:1 or greater than 0.19:1 e.g., 0.07:1, 0.08:1, 0.20:1, 0.21:1.

In accordance with a further aspect of the exemplary embodiment, a ratio of the depth 24 to the overall longitudinal length 28 of the screw extracting tip 16 for each screw thread 18A-C ranges from about 0.05:1 to 0.10:1, but can alternatively be less than 0.05:1 or greater than 0.10:1 e.g., 0.03:1, 0.04:1, 0.11:1, 0.12:1.

In accordance with another aspect of the exemplary embodiment, a distal end of the screw extracting tip 16 has an overall diameter 30 of about 0.19 inches, and an overall longitudinal length of about 1.3 times the overall diameter of the distal end. The screw extracting tip 16 further includes first, second and third screw threads, wherein each screw thread has a pitch of about 0.21 times the overall diameter of the distal end, a lead of about 0.64 times the overall diameter of the distal end, and a depth of about 0.13 times the overall diameter of the distal end.

In accordance with yet another aspect of the exemplary embodiment, the screw extracting tip 16 has an overall diameter 30 of about 0.19 inches, and an overall longitudinal length of about 1.3 times the overall diameter of the distal end. The screw extracting tip 16 further includes first, second and third screw threads, wherein each screw thread has a lead of about 0.12 inches, a pitch of about 0.04 inches, and a depth of about 0.02 inches.

In operation, the orthopedic screw extractor 10 can be used with a standard drill interface or handle interface. Specifically, a handle or tool, e.g., a drill, is attached to the end portion 14 of the orthopedic screw extractor 10 before insertion of the screw extracting tip 16 in the hole of the fastener or screw to facilitate rotation of the orthopedic screw extractor 10. The orthopedic screw extractor 10 can be used with a drill via a Hudson extractor adapter for connecting to a standard Hudson connector found on most surgical drills. Similarly, the orthopedic screw extractor 10 can be used with a ratcheting T-handle for removing a screw manually.

After the orthopedic screw extractor 10 is connected to the tool (or handle), the screw extracting tip 16 is inserted into a hole drilled into a fastener or screw that is stripped or broken. The screw extracting tip 16 is inserted deep enough such that the screw threads 18A-C engage the sides of the hole.

Then, the orthopedic screw extractor 10 is turned in a counter clockwise direction over the screw to be extracted until the screw threads 18A-C on the screw extracting tip 16 engage and lock onto the screw. The specific tapering of the screw extracting tip 16 is particularly advantageous since it provides greater threaded surface area over a longitudinal depth of the screw extracting tip compared to conventional orthopedic screw extractors. As a result, the orthopedic screw extractor 10 has a stronger grip on a screw during extraction. Preferably, the flutes 26A-C may be arranged in a clockwise manner for removal of left hand thread screws. Alternatively, the flutes 26A-C can be arranged counter-clockwise to remove right hand thread screws.

The screw threads 18A-C of the screw extracting tip 16 cut a spaced spiral thread into the sides of the hole of the screw. The screw threads 18A-C bite into the sides of the screw lodging the orthopedic screw extractor 10 firmly into a head of the screw. Each of the screw threads 18A-C are configured such that screw extracting tip 16 maximizes engagement of the screw threads 18A-C to the fastener or screw being extracted. This is accomplished by the narrow taper angle, the buttress thread and the coating applied to the screw threads 18A-C on the screw extracting tip. As a result, the screw threads 18A-C are secured to the fastener or screw being removed. The screw is removed by continued rotation of the orthopedic screw extractor 10 in a counter clockwise direction. Specifically, rotation of the orthopedic screw extractor 10 exerts a counter clockwise torque until the screw or fastener is removed.

Generally, the orthopedic screw extractor 10 is aligned axially with a generally hexagonal shaped screw well of a fastener or screw. However, it is contemplated that a drill bit may be used to remove the head off of a stripped screw or to drill a hole into a well of the screw to be extracted in order to facilitate better grip and seating of the orthopedic screw extractor 10 to the screw being extracted. For example, drilling a head off of a screw can facilitate extraction of locking plate screws that have been cold welded onto a plate.

In sum, the orthopedic screw extractor 10 advantageously allows a surgeon to effectively and efficiently remove a screw from a patient while minimizing bone loss. As discussed above, the narrow taper angle, the buttress thread and the coating applied to the screw threads allows the orthopedic screw extractor to lock onto the fastener or screw being removed. As a result, more torque is applied to facilitate removal of the stripped screw or fastener. In conventional orthopedic screw extractors, multiple attempts to lock onto the stripped screw or fastener can lead to additional stress on the surrounding bone area leading to increased bone loss. Moreover, the length of the orthopedic screw extractor 10 provides better visibility for a surgeon extracting a screw and allows for minimally invasive surgical procedures. Preferably, the orthopedic screw extractor 10 has an overall length of about 6 inches, but can alternatively be less than or greater than 6 inches e.g., 4, 5, 7, 8 inches. In accordance with an aspect, the orthopedic screw extractor 10 may be used with an extension which is particular advantageous when the screw or fastener to be removed is deeply embedded in a patient.

Moreover, the cannulation 136 facilitates positioning of the orthopedic screw extractor 10. Specifically, the cannulation 136 allows a surgeon to follow a guide wire, e.g., a k-wire, down to a screw embedded in the bone of a patient and facilitates positioning of the orthopedic screw extractor 10 into a hole of a stripped or damaged screw.

Advantageously, the screw extracting tip 16 of the present invention maximizes engagement of the screw threads with a screw or fastener being extracted. As a result, the orthopedic screw extractor 10 locks onto the screw and facilitates efficient removal of the screw during an extraction procedure. Preferably, the orthopedic screw extractor should engage as much of an interior surface of a screw so as to decrease the likelihood of a spinoff of the device from the fastener while providing a stronger grip on a screw being extracted. The screw extracting tip 16 has a narrow shape allowing for more screw threads to enter the hole of a screw being removed and to provide additional torque during extraction. Additionally, the narrow shape allows a surgeon to extract a pedicle screw more efficiently because the orthopedic screw extractor can be positioned between saddles of the pedicle screw.

Attached as TABLE 2 is a cross sectional area of each screw thread of several exemplary embodiments of the orthopedic screw extractor described above in relation to conventional designs, wherein the dimensions of each orthopedic screw extractor set forth correspond to various screw sizes. In comparison to conventional designs, the increased cross sectional area of the screw threads 18A-C in the present invention maximizes engagement of the screw threads with a screw or fastener being extracted. As a result, the increased cross sectional area of each screw thread provides a stronger grip on a screw or fastener being extracted.

TABLE 2

| | Cross Sectional Area of Each Screw Thread (in$^2$) | | |
| --- | --- | --- | --- |
| | 3 mm Extractor | 5 mm Extractor | 7 mm Extractor |
| Conventional Design | 0.00011 | 0.00025 | 0.00025 |
| Present Invention | 0.00013 | 0.00042 | 0.00042 |
| % Increase | 18.2% | 68% | 68% |

While the present invention has been described with reference to preferred embodiments, it will be appreciated by those skilled in the art that various changes may be made and equivalents may be substituted for elements thereof without departing from the scope of the present invention. In addition, modifications may be made to adapt a particular situation or material to the teachings of the present invention without departing from the essential scope thereof. It is to be understood, therefore, that the present invention not be limited to the particular embodiments disclosed, but it is intended to cover modifications within the spirit and scope of the present invention as disclosed.

We claim:

1. An orthopedic screw extractor comprising:
   a shaft;
   an end portion about a first end of the shaft for securing to a handle; and
   a screw extracting tip about a second end of the shaft opposite the first end, the screw extracting tip having:
   a frustoconical shape having a side at a taper angle α of about 5 to 15 degrees relative to a longitudinal axis of the screw extracting tip, and
   screw threads including:
   a lead of about 0.04 to 0.14 inches,
   a pitch of about 0.01 to 0.05 inches, and
   a depth of about 0.004 to 0.03 inches.

2. The orthopedic screw extractor of claim 1, wherein the screw extracting tip further includes flutes circumferentially spaced about the screw extracting tip and extending across an entire length of the screw extracting tip.

3. The orthopedic screw extractor of claim 2, wherein the flutes include a major planar surface and a cutting surface at an angle from the major planar surface of about 50 to 70 degrees.

4. The orthopedic screw extractor of claim 1, wherein the screw extracting tip has an overall longitudinal length of about 0.20 to 0.32 inches.

5. The orthopedic screw extractor of claim 1, wherein a distal end of the screw extracting tip has an overall diameter of about 0.05 to 0.29 inches.

6. The orthopedic screw extractor of claim 5, wherein the lead of the screw threads is about 0.05 to 0.09 inches and the overall diameter of the distal end is about 0.05 to 0.16 inches, or wherein the lead of the screw threads is about 0.10 to 0.14 inches and the overall diameter of the distal end is about 0.16 to 0.29 inches.

7. The orthopedic screw extractor of claim 5, wherein the pitch of the screw threads is about 0.01 to 0.03 inches and the overall diameter of the distal end is about 0.05 to 0.16 inches, or wherein the pitch of the screw threads is about 0.03 to 0.05 inches and the overall diameter of the distal end is about 0.16 to 0.29 inches.

8. The orthopedic screw extractor of claim 5, wherein the depth of the screw threads is about 0.005 to 0.015 inches and the overall diameter of the distal end is about 0.05 to 0:16 inches, or wherein the depth of the screw threads is about 0.01 to 0.03 inches and the overall diameter of the distal end is about 0.16 to 0.29 inches.

9. The orthopedic screw extractor of claim 1, wherein a ratio of the lead to the pitch is about 3:1.

10. The orthopedic screw extractor of claim 1, wherein a ratio of the pitch to the depth is about 1.9:1 to about 1.7:1.

11. The orthopedic screw extractor of claim 1, wherein a ratio of the depth to an overall diameter of a distal end of the screw extracting tip is about 0.09:1 to about 0.19:1.

12. The orthopedic screw extractor of claim 1, wherein a ratio of the depth to an overall longitudinal length of the screw extracting tip is about 0.05:1 to about 0.10:1.

13. The orthopedic screw extractor of claim 1, wherein the screw extracting tip has a coating selected from the group consisting of titanium nitride or aluminum titanium nitride.

14. The orthopedic screw extractor of claim 1, further comprising a cannulation extending along a longitudinal axis of the shaft.

15. The orthopedic screw extractor of claim 14, wherein the cannulation extends through the screw extracting tip forming an opening about a distal face of the screw extracting tip.

16. The orthopedic screw extractor of claim 14, wherein the cannulation has an overall diameter of about 0.04 to 0.11 inches.

17. An orthopedic screw extractor comprising:
   a shaft;
   an end portion about a first end of the shaft for securing to a handle; and
   a screw extracting tip about a second end of the shaft opposite the first end, the screw extracting tip having:
   a frustoconical shape having a side at a taper angle α of about 10 degrees relative to a longitudinal axis of the screw extracting tip,
   a distal end having an overall diameter of about 0.19 inches, and
   first and second screw threads, each screw thread including:
   a lead of about 0.12 inches,
   a pitch of about 0.04 inches,
   a thread angle β of about 45 degrees, and
   a depth of about 0.02 inches.

18. The orthopedic screw extractor of claim 17, wherein the screw extracting tip further includes first and second flutes circumferentially spaced about the screw extracting tip and extending across an entire length of the screw extracting tip.

19. An orthopedic screw extractor comprising:
   a shaft;
   an end portion about a first end of the shaft for securing to a handle; and
   a screw extracting tip about a second end of the shaft opposite the first end, the screw extracting tip having:
   a frustoconical shape having a side at a taper angle α of about 10 degrees relative to a longitudinal axis of the screw extracting tip,
   a distal end having an overall diameter of about 0.19 inches,
   an overall longitudinal length of about 1.3 times the overall diameter of the distal end, and
   screw threads including:
   a pitch of about 0.2 times the overall diameter of the distal end,
   a lead of about 0.6 times the overall diameter of the distal end,
   a thread angle β of about 45 degrees, and
   a depth of about 0.1 times the overall diameter of the distal end.

20. The orthopedic screw extractor of claim 19, wherein the screw extracting tip further includes flutes circumferentially spaced about the screw extracting tip and extending across the length of the screw extracting tip.

21. The orthopedic screw extractor of claim 1, wherein the screw threads include a thread angle β of about 40 to 50 degrees.

* * * * *